(12) United States Patent
Haskell et al.

(10) Patent No.: US 11,282,589 B2
(45) Date of Patent: Mar. 22, 2022

(54) SYNTHESIZING COMPLEX POPULATION SELECTION CRITERIA

(71) Applicant: IMS Health Incorporated, Danbury, CT (US)

(72) Inventors: Thomas Paul Haskell, Havertown, PA (US); Benjamin Alexander Paul Hughes, London (GB)

(73) Assignee: IQVIA Inc., Durham, NC (US)

( * ) Notice: Subject to any disclaimer, the term of this patent is extended or adjusted under 35 U.S.C. 154(b) by 620 days.

(21) Appl. No.: 14/506,961

(22) Filed: Oct. 6, 2014

(65) Prior Publication Data
US 2016/0098541 A1 Apr. 7, 2016

(51) Int. Cl.
*G16H 10/20* (2018.01)
*G16Z 99/00* (2019.01)

(52) U.S. Cl.
CPC ............. *G16H 10/20* (2018.01); *G16Z 99/00* (2019.02)

(58) Field of Classification Search
None
See application file for complete search history.

(56) References Cited

U.S. PATENT DOCUMENTS

| | | | | |
|---|---|---|---|---|
| 8,880,547 B1* | 11/2014 | Mills | ................. | G06F 17/30672 707/767 |
| 2004/0068488 A1* | 4/2004 | Dettinger | .......... | G06F 17/30395 |
| 2009/0138435 A1* | 5/2009 | Mannion | ........... | G06F 17/30554 |
| 2011/0231422 A1* | 9/2011 | Rawlings | ............. | G06F 19/3487 707/758 |
| 2012/0078659 A1* | 3/2012 | Ashrafzadeh | .......... | G06Q 50/22 705/3 |
| 2014/0337272 A1* | 11/2014 | Cox | ....................... | G06N 5/025 706/47 |

OTHER PUBLICATIONS

Kadioglu et al., "Efficient Search Procedures for Solving Combinatorial Problems", May 2012, Brown University, https://cs.brown.edu/research/pubs/theses/phd/2012/kadioglu.pdf (Year: 2012).*

* cited by examiner

*Primary Examiner* — Devin C Hein
(74) *Attorney, Agent, or Firm* — John Maldjian; Patrick Garrett; Stevens & Lee PC

(57) ABSTRACT

System and method to determine a reduced cohort criteria, the method including: defining N selection criteria to select a cohort from among a universe of patient data; querying a patient database, by use of a processor, and by use of the N selection criteria, in order to define a full patient population; selecting a subset of size M of the N selection criteria, to produce a subset criteria; selecting a permutation of the subset criteria, to produce a permuted subset criteria in a predetermined order; for each member of the permuted subset criteria: querying the patient database by use of the member of the permuted subset criteria to produce a respective interim patient population; combining all respective interim patient populations to produce a partial patient population; and calculating, by a processor, a coverage figure of merit that compares the partial patient population to the full patient population.

12 Claims, 5 Drawing Sheets

Real World Explorer – Cohort Detailed Description.

Generated on: 6/6/2014 3:59:26 PM

---

Sample 1.
United States – PharMetrics Plus.
(Assigned Disease: Rheumatoid Arthritis.)

Cohort Summary:

Cohort ID:
   Cohort Name: Sample 1.
   Cohort Description:
   Created By: Tom Haskell
   Country: United States
   Data Source: PharMetrics Plus

Query Time Frame and Disease:

Cohort Time Frame: July 2011 to December 2011.
   Assigned Disease: Rheumatoid Arthritis.

Query Details:

Filter – Diagnoses:
   Diagnosis Codes: DIAG_CD = 714.0, 714.1, 714.2, 714.30, 714.31, 714.81.
   Diagnosis Types: Primary, Other.
   Custom Time Frame: Not Set.
   Evaluation Type: Only one Code needed to Match.

Filter – Enrollment:
   Continuous Enrollment: Patients must be continuously enrolled for entire filter period.
   Custom Time Frame: January 2011 – December 2011.

Filter - Patient Gender:
   Include Male Patients: Yes
   Include Female Patients: Yes
   Include Unknown Patients: No.

Output Time Frame:

Output Time Frame: July 2011 to December 2011.

Transaction File Selections:

Transaction – Diagnosis.
   Transaction – Drug Treatment.
   Transaction – Medical Procedure.
   Transaction – Stay.
   Reference – Patient.

Real – World Reporting Selections:

Report: Patient Count Breakout.

Notification Options:

Email To: bcrandall@us.imshealth.com.
   Email CC:

Example of current attrition deliverable – US medical claims

Source: US Medical Claims (DX)

Patients remaining MAT 06/2012    ims

| | Basis: all included patients (crit. 1-4) | | Basis: all asthma patients aged 12-17 years (crit. 1-2) | |
|---|---|---|---|---|
| Inclusion criteria: | | | | |
| 1. Diagnosis Asthma | 6,497,561 | 100.0% | | |
| 2. Age 10-17 years at time point of diagnosis | 663,090 | 10.3% | 663,090 | 100.0% |
| 3. ICS or fluticasone | 76,813 | 1.2% | 76,813 | 11.6% |
| 4. LABA, LAMA, LTRA, theophylline | 24,755 | 0.38% | 100.0% | 74,902 | 11.3% |
| Exclusion criteria: | | | | |
| 1. Corticosteroid Therapy | 24,021 | 0.37% | 97.03% | 645,880 | 97.4% |
| 2. Tuberculosis | 24,013 | 0.37% | 97.00% | 645,699 | 97.4% |
| 3. Immunodeficiency (incl. HIV) | 23,864 | 0.37% | 96.40% | 643,432 | 97.0% |
| 4. Hepatitis and/or liver cirrhosis | 23,841 | 0.37% | 96.31% | 642,901 | 97.0% |
| 5. Cystic Fibrosis | 23,807 | 0.37% | 96.17% | 642,317 | 96.9% |
| 6. Malignancy | 23,625 | 0.37% | 95.44% | 636,606 | 96.0% |
| 7. Immunosuppressive Therapy | | 0.00% | 0.00% | | 0.0% |
| 8. Biologic Treatment | 23,624 | 0.37% | 95.43% | 636,578 | 96.0% |
| 9. Roflumilast | | 0.00% | 0.00% | | 0.0% |
| 10. Allergene | | 0.00% | 0.00% | | 0.0% |
| 11. Vaccine | 13,632 | 0.21% | 55.07% | 380,672 | 57.4% |
| 12. Female patients pregnant or lactating | | 0.00% | 0.00% | | 0.0% |

SYNTHESIZING COMPLEX POPULATION SELECTION CRITERIA

BACKGROUND

Field of the Invention

Embodiments of the present invention generally relate to observational testing, and, in particular, to a system and method for post-selection determination of criteria for membership in an observational test.

Description of Related Art

Observational studies are an important category of study designs. For some kinds of investigative questions (e.g., related to plastic surgery), randomized controlled trials may not always be indicated or ethical to conduct. Instead, observational studies may be the next best method to address these types of questions. Well-designed observational studies may provide results similar to randomized controlled trials, challenging the belief that observational studies are second-rate. Cohort studies and case-control studies are two primary types of observational studies that aid in evaluating associations between diseases and exposures.

Well-designed randomized controlled trials (RCTs) have held the pre-eminent position in the hierarchy of evidence-based medicine (EBM) as level I evidence. However, RCT methodology, which was first developed for drug trials, can be difficult to conduct for some investigations (e.g., surgical cases). Instead, well-designed observational studies, recognized as level II or III evidence, can play an important role in deriving evidence for such investigations. Results from observational studies are often criticized for being vulnerable to influences by unpredictable confounding factors. However, comparable results between observational studies and RCTs are achievable. Observational studies can also complement RCTs in hypothesis generation, establishing questions for future RCTs, and defining clinical conditions.

Observational studies fall under the category of analytic study designs and are further sub-classified as observational or experimental study designs. The goal of analytic studies is to identify and evaluate causes or risk factors of diseases or health-related events. The differentiating characteristic between observational and experimental study designs is that in the latter, the presence or absence of undergoing an intervention defines the groups. By contrast, in an observational study, the investigator does not intervene and rather simply "observes" and assesses the strength of the relationship between an exposure and disease variable. Three types of observational studies include cohort studies, case-control studies, and cross-sectional studies. Case-control and cohort studies offer specific advantages by measuring disease occurrence and its association with an exposure by offering a temporal dimension (i.e. prospective or retrospective study design). Cross-sectional studies, also known as prevalence studies, examine the data on disease and exposure at one particular time point. Because the temporal relationship between disease occurrence and exposure cannot be established, cross-sectional studies cannot assess the cause and effect relationship.

The word "cohort" is used in epidemiology to define a set of people followed over a period of time. In particular, "cohort" refers to a group of people with defined characteristics who are followed up to determine incidence of, or mortality from, some specific disease, all causes of death, or some other outcome.

A well-designed cohort study can provide powerful results. In a cohort study, an outcome-free or disease-free study population is first identified by the exposure or event of interest, and then is followed in time until the disease or outcome of interest occurs. Because exposure is identified before the outcome, cohort studies have a temporal framework to assess causality and thus have the potential to provide the strongest scientific evidence. A cohort study is particularly advantageous for examining rare exposures because subjects are selected by their exposure status, and rates of disease may be calculated in exposed and unexposed individuals over time (e.g. incidence, relative risk). Additionally, an investigator can examine multiple outcomes simultaneously. However, the cohort study may be susceptible to selection bias. A cohort study may be large, particularly to study rare exposures, and require a large sample size and a potentially long follow-up duration of the study design, resulting in a costly endeavor.

Cohort studies may be prospective or retrospective. Prospective studies are carried out from the present time into the future. Because prospective studies are designed with specific data collection methods, it has the advantage of being tailored to collect specific exposure data and may be more complete. A disadvantage of a prospective cohort study may include the long follow-up period while waiting for events or diseases to occur. Thus, this study design is inefficient for investigating diseases with long latency periods and is vulnerable to a high loss to follow-up rate.

In contrast, retrospective cohort studies are better indicated for timely and inexpensive study design. Retrospective cohort studies, also known as historical cohort studies, are carried out at the present time and look to the past to examine medical events or outcomes. A cohort of subjects, selected based on exposure status, is chosen at the present time, and outcome data (i.e. disease status, event status), which was measured in the past, are reconstructed for analysis. An advantage of the retrospective study design analysis is the immediate access to the data. The study design is comparatively less costly and shorter than prospective cohort studies. However, disadvantages of retrospective study design include limited control the investigator has over data collection. The existing data may be incomplete, inaccurate, or inconsistently measured between subjects, for example, by not being uniformly recorded for all subjects.

Conventionally, a cohort study defines the selected group of subjects by predetermined criteria (e.g., exposure to a substance, or having a particular medical condition, etc.) at the start of the investigation. A critical characteristic of subject selection is to have both the exposed and unexposed groups be selected from the same source population. Subjects who are not at risk for developing the outcome should be excluded from the study. The source population is determined by practical considerations, such as sampling. Subjects may be effectively sampled from the hospital, be members of a community, or from a doctor's individual practice. A subset of these subjects will be eligible for the study.

Attempts have been made and have failed to adequately address the calculation of inferred selection criteria from an observed population. Attempts in the background art generally involve use set theory visualization to compare population across two attributes or data variables. However, when population selection may involve as many as 20-40 attributes, a set theory approach lacks scalability. Known solutions only allow comparison of two variables at a time and do not perform a population synthesis. Manual efforts to expand the analysis beyond two variables has many drawbacks, such as requiring costly expert labor to synthesize queries, being relatively slow, and is not adaptable to allow non-technical business users themselves to derive insights from large healthcare datasets.

However, such selection methods for a retrospective cohort study may suffer from limited sample size or selection bias. Therefore, what is needed is to combine the advantages of a retrospective cohort study without the disadvantages of limited sample size or selection bias.

SUMMARY

Embodiments in accordance with the present disclosure provide a systematic process to determine the most significant factors that can be used to approximate a patient population group.

Embodiments in accordance with the present disclosure provide a method to determine a reduced cohort criteria, the method including: defining N selection criteria to select a cohort from among a universe of patient data; querying a patient database, by use of a processor coupled to the patient database, and by use of the N selection criteria, in order to define a full patient population; selecting a subset of size M of the N selection criteria, to produce a subset criteria; selecting a permutation of the subset criteria, to produce a permuted subset criteria in a predetermined order; for each member of the permuted subset criteria: querying the patient database by use of the member of the permuted subset criteria to produce a respective interim patient population; combining all respective interim patient populations to produce a partial patient population; and calculating, by a processor, a coverage figure of merit that compares the partial patient population to the full patient population.

A system to determine a reduced cohort criteria, the system including: a communication interface to allow a human to define N selection criteria used to select a cohort from among a universe of patient data; a processor coupled to a patient database, the processor configured to query the patient database and by use of the N selection criteria, in order to define a full patient population; a selection module coupled to the processor, the selection module configured to select a subset of size M of the N selection criteria, to produce a subset criteria; a selection module coupled to the processor, the selection module configured to select a permutation of the subset criteria, to produce a permuted subset criteria in a predetermined order; for each member of the permuted subset criteria: querying the a patient database by use of the member of the permuted subset criteria to produce a respective interim patient population; combining all respective interim patient populations to produce a partial patient population; and calculating, by a processor, a coverage figure of merit that compares the partial patient population to the full patient population.

The preceding is a simplified summary of embodiments of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings wherein like reference numerals in the various figures are utilized to designate like components, and wherein:

FIG. 4 illustrates a user interface presented to a user to show selection criteria chosen by a user; and FIG. 5 illustrates a user interface presented to a user to show a result of a simulation using a selected subset and permutation of the selection criteria.

Figure 1:
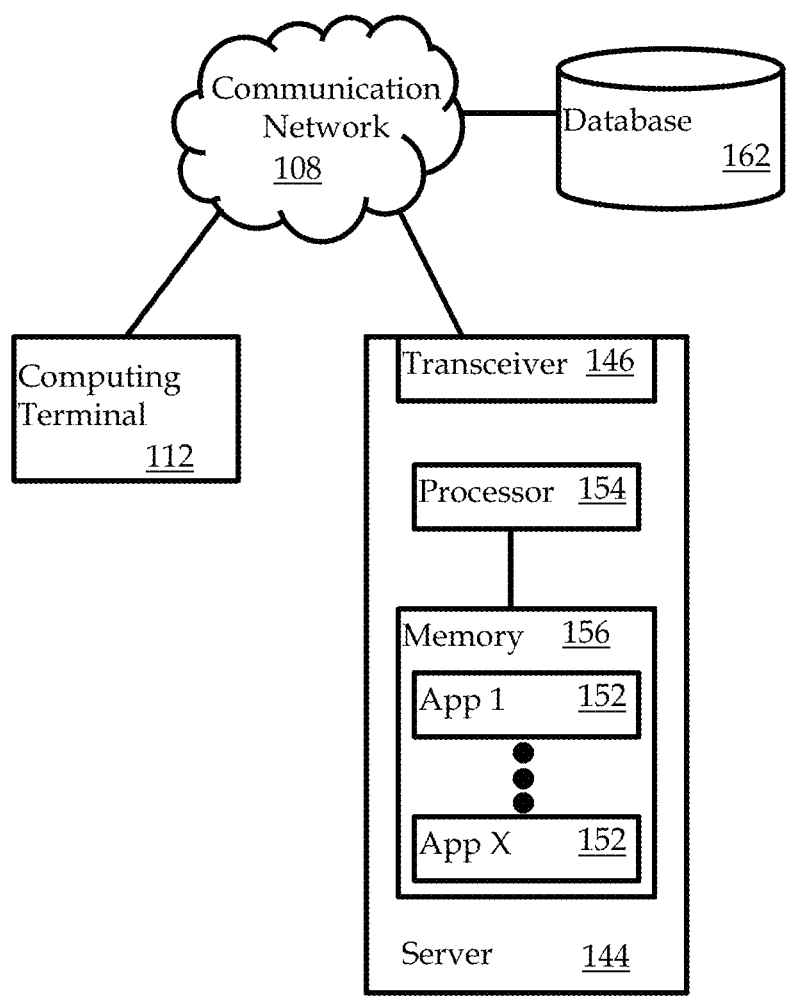
FIG. 1 depicts a system according to an embodiment of the present disclosure.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The disclosure will be illustrated below in conjunction with an exemplary digital information system. Although well suited for use with, e.g., a system using a server(s) and/or database(s), the disclosure is not limited to use with any particular type of system or configuration of system elements. Those skilled in the art will recognize that the disclosed techniques may be used in any system or process in which it is desirable to provide a transferable permission to access information or control a decision.

The exemplary systems and methods of this disclosure will also be described in relation to software, modules, and associated hardware. However, to avoid unnecessarily obscuring the present disclosure, the following description omits well-known structures, components and devices that may be shown in block diagram form, are well known, or are otherwise summarized.

In the following detailed description, numerous specific details are set forth in order to provide a thorough understanding of embodiments or other examples described herein. In some instances, well-known methods, procedures, components and circuits have not been described in detail, so as to not obscure the following description. Further, the examples disclosed are for exemplary purposes only and other examples may be employed in lieu of, or in combination with, the examples disclosed. It should also be noted the examples presented herein should not be construed as limiting of the scope of embodiments of the present invention, as other equally effective examples are possible and likely.

As used herein, the term "module" refers generally to a logical sequence or association of steps, processes or components. For example, a software module may comprise a set of associated routines or subroutines within a computer program. Alternatively, a module may comprise a substantially self-contained hardware device. A module may also comprise a logical set of processes irrespective of any software or hardware implementation.

As used herein, the term "transmitter" may generally comprise any device, circuit, or apparatus capable of transmitting a signal. As used herein, the term "receiver" may generally comprise any device, circuit, or apparatus capable of receiving a signal. As used herein, the term "transceiver" may generally comprise any device, circuit, or apparatus capable of transmitting and receiving a signal. As used herein, the term "signal" may include one or more of an electrical signal, a radio signal, an optical signal, an acoustic signal, and so forth.

The term "computer-readable medium" as used herein refers to any tangible storage and/or transmission medium that participate in storing and/or providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, RAM, PROM, EPROM, FLASH-EPROM, solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

At the present time, large-scale routine healthcare databases are amassed and maintained based upon data gathered by healthcare providers and healthcare insurers. For example, a patient who submits to routine health care such as a yearly checkup, regularly-scheduled pap smears or mammograms, or visits for acute but relatively minor problems such as an infection, stitches, or broken bone, will have associated with them a series of healthcare records over time. Healthcare records may also include information related to non-routine care such as emergency room visits, hospital admissions, or other serious healthcare events. The healthcare records may document the progress over time of chronic conditions such as cholesterol levels, high blood pressure, and the like. The healthcare records may also include demographic information such as age, ethnicity, height, weight, and so forth. Because a large portion of the population has access to and uses health care, and the portion is likely to grow in future years due to the Affordable Care Act, such data is a vast source of information over a large portion or cross-section of the population, representing persons of many different characteristics, risk factors, and so forth. The data for any individual patient may also be available over an extended period of time such as a period of years, so that changes in slowly-progressing medical conditions or slowly-changing patient characteristics may be captured by the data.

In the United Kingdom (UK), such healthcare records may include sources such as the Clinical Practice Research Datalink (CPRD), General Practice Research Database (GPRD), primary care database (GOLD), the hospital episode statistics (HES) and the Office for National Statistics (ONS) mortality data.

For example, the GPRD, established in the UK in 1987, is a medical records database that general practitioners (GPs) use as the primary means of tracking patient clinical information. The total population in the GPRD exceeds nine million patients with over 35 million person-years of follow-up between 1987 and 2002. About 5% of the UK population is in the GPRD, which is broadly representative of the general UK population in terms of age, sex and geographic distribution. The GPRD, which contains information on diagnoses and medications, was established with the intent of allowing researchers to conduct high quality epidemiologic studies and has been used in more than 200 peer-reviewed publications. All information is recorded by the GP or a member of the office staff as part of the patient's medical record. Approximately 1,500 general practitioners representing 500 practices across the UK participated in the GPRD between 1987 and 2001. GPs are trained in data entry and their data are reviewed by administrators at the GPRD to ensure that they are of sufficient quality for research studies.

Healthcare analysis and research increasing may rely upon the use of such large-scale routine healthcare databases, in particular for retrospective cohort studies. Such databases, because of the coverage over a large portion or cross-section of the population, representing persons of many different characteristics, risk factors, and so forth, may reduce the drawbacks of traditional retrospective cohort studies such as existing data being incomplete, inaccurate, or inconsistently measured between subjects, for example, by not being uniformly recorded for all subjects. Standardized tests for blood work, pap smear, and other routine procedures encourage uniformity and completeness of monitored healthcare parameters.

To work with large-scale routine healthcare databases for any use, the definition of the relevant population under study is the first step and an important step. There may be more than one relevant population, for example, a first population that has developed a particular condition, and a second population that has not developed the particular condition as of the time of selection. The selection criteria form an important part of protocols (i.e., population criteria and analysis plan) used for clinical trial and health outcomes studies.

The selection criteria may be referred to as a scenario. A scenario may be known as a set of instructions used to define a patient cohort or subpopulation from a database. A series of scenarios may be known as a group of sets of instructions. Running a scenario may be known as the computational process of applying a set of instructions to a database. For example, suppose a database contains information about a large number of patients with asthma. Further suppose that we want to study patients who were originally diagnosed with asthma as children. However, suppose we need to better define the term "child", because a patient diagnosed as a teenager may be medically treated differently than a patient diagnosed earlier than age 12. Therefore, we may run a few scenarios in order to test for an appropriate age range. In a first scenario, we may include everybody diagnosed under 18 years of age. In a second scenario, we may include everybody between 3-17 years old. In a third scenario, we may include everybody between 12-17. Thus, we may have a set of three different scenarios. Sending the instruction of "Return every patient in the age range X-Y" to the database is an example of the process of running the scenario.

Patient characteristics may be represented as a multi-dimensional vector or matrix. Patient characteristics may include sociodemographic factors (e.g., age, sex, place of residence, etc.), clinical factors (e.g., comorbidities, medical history, genetic history, blood type, medications used in the week prior to presentation, functional status, immunization history, smoking status, drinking status, etc.), and laboratory data. Dozens of characteristics may be relevant or possibly relevant. Relevancy may be dependent upon the type of study, and may be informed by existing medical knowledge. For example, patient weight may be more relevant to a diabetes study than patient eye characteristics, but patient eye characteristics may have more relevance to a study of eye disease.

Each patient characteristic over a population of patients may be expressed as a statistic that represents the population as a whole. For example, the statistic may be in a form such as a histogram, a series of numeric ranges (e.g., 40-50 years old; 50-60 years old; 150-160 lbs; 160-170 lbs; etc), a series of qualitative ranges (e.g., non-drinker vs. social drinker vs. heavy drinker, etc.), and so forth. Other mathematical representations of the multi-dimensional vector or matrix may be possible. Patient characteristics may not be independent of each other, e.g., selection of a female gender characteristic may result in a smaller and lighter population of patients compared to a selection of a male gender characteristic. The data is complex and highly dimensional. Researchers have to make assumptions, based upon science, intuition or other data analysis, that involve structure that is believed to exist in the data but that cannot be observed directly. The data sets are large and growing with a never-ending stream of new data.

Some patients may be classified by use of one or more population codes. The population codes, in turn, represent characteristics of interest to a retrospective cohort study. For example, one population coding system is ICD-10, which is the 10th revision of the International Statistical Classification of Diseases and Related Health Problems (ICD), a medical classification list by the World Health Organization (WHO). ICD-10 codes for diseases, signs and symptoms, abnormal findings, complaints, social circumstances, and external causes of injury or diseases. The code set allows more than 14,400 different codes and permits the tracking of many new diagnoses. The codes can be expanded to over 16,000 codes by using optional sub-classifications. The detail reported by ICD can be further increased, with a simplified multi-axial approach, by using codes meant to be reported in a separate data field.

Another population coding system is the Read code, which is the standard clinical terminology system used in General Practice in the United Kingdom (UK). Read codes support detailed clinical encoding of multiple patient phenomena including: occupation; social circumstances; ethnicity and religion; clinical signs, symptoms and observations; laboratory tests and results; diagnoses; diagnostic, therapeutic or surgical procedures performed; and a variety of administrative items (e.g. whether a screening recall has been sent and by what communication modality, or whether an item of service fee has been claimed). It therefore includes but goes significantly beyond the expressivity of a diagnosis coding system.

However, there are major barriers to usage of coding systems for patient characteristics and capturing classification value from large-scale routine healthcare databases. Due the complex nature of population codes used to define populations, conventional practice has been that only experts in the use of large healthcare datasets, who possess technical skills with respect to statistical software concepts and usage, can manually define and understand such population codes in practice.

Conventionally, synthesis of population selection rules also must be performed manually by such an expert. Synthesis is known as a process of reducing from potentially hundreds of patient population codes to a much smaller set of medical factors, the factors being referred to as inclusion factors or exclusion factors. For example, for a predetermined asthma population (e.g., patients that were initially diagnosed between 12-17 years of age) a medical researcher may decide to look at only patients who were treated with either of two drugs: inhaled corticosteroids (ICS) or fluticasone (i.e., an example of an inclusion criterion). Each of those drugs will have a specific code which usually less recognizable to medical researchers than the drug name itself. In addition to looking at these drugs, a medical researcher may also set another rule to study only patients who were treated in a primary care setting. However, in practice a rule to narrow a study only to patients who were treated in a primary care setting may not be significant because virtually all asthma patients are treated in a primary care setting and thus fails to narrow the population much in practice. Manual synthesis may fail to recognize that such a rule is not significantly meaningful. Thus, manual synthesis may include such a criterion whereas an automated method may recognize that the criterion is not significantly meaningful and thus would not include the criterion in a summary.

Inclusion factors refer to the medical factors whose presence is most highly correlated (e.g., in a mathematical sense) with the selected patients. Exclusion factors refer to the medical factors whose absence is most highly correlated with the selected patients. Inclusion and exclusion factors may be scaled to a mathematical range, e.g., [−1.0, 1.0] for a mathematical correlation, or [0%, 100%], and so forth. Inclusion and exclusion factors when interpreted may be normalized to their presence in a population of patients, e.g., an unnormalized inclusion factor of 20% may be more significant after normalization if a different group (e.g., a control group or the general population) contain a much smaller number (e.g., 1%) of members who share that factor. Manual synthesis may represent days or weeks of effort, depending upon the size of the study. Persons who possess such skills are scarce in many countries. Therefore, a need exists for systems that can analyze population groups in an automated manner, with little to no input required of a human expert.

Manual synthesis may result in a large number of rules (i.e., inclusion and exclusion criteria) that are used, even though only a few criteria have significant impact on the population selection. A large number of criteria that have little impact to patient selection may tend to obscure insights gained from consideration of just the most significant criteria, in which significance is determined by how much the patient population is narrowed.

Embodiments in accordance with the present disclosure improve on this manual synthesis. The number of patients in the final cohort will stay identical and is independent of the order in which the criteria are applied. However, the present Applicants have discovered that the different criteria may have different impacts depending on the sequence of application. For a first example, suppose we are studying female breast cancer and the first criterion we apply a gender criterion to produce an immediate 50% reduction in the population. In contrast, for a second example suppose that the first criterion we apply to the population is "Diagnosis: Breast cancer" and then we apply as a second criterion the gender specification "Women." In the second example, the gender specification would have hardly any impact on the size of the overall cohort, because even though breast cancer in men is not unknown, breast cancer is overwhelmingly more prevalent in women than in men.

More generally, when a population (i.e., a patient cohort) is constructed, embodiments in accordance with the present disclosure may test various combinations of the patient population codes and/or their associated patient criteria on a dataset through simulations to find out which inclusion and exclusion criteria drove the majority of the selection. The simulation is the process of defining the key criteria ranking. In contrast, synthesis builds upon simulation by also including the decision of which factors to show in an output (e.g., for a human researcher). The automated synthesis may take from hours to days of simulation work, but may save days to weeks of manual synthesis, and furthermore may allow for the analysis of additional scenarios that could not feasibly be analyzed by manual methods within a desired analytic timeframe. The simulation results may be saved for future or off-line analysis.

Embodiments in accordance with the present disclosure may further synthesize in an automated manner, and through intuitive visual representation, the most critical rules, which hither-to had to be conducted by experienced experts.

Criteria may be combined using a combination of both Boolean "AND" and Boolean "OR" operations. For example, suppose the total patient population may be defined by the five criteria: ("A" and "B" and "C" and ("D" or "E")). In a reduced set of criteria, omitting one of the "AND" factors (e.g., use only: ("B" and "C" and ("D" or "E")), results in a larger set than the total patient population we are trying to emulate, i.e., over-inclusion. Omitting one of the "OR" factors (e.g., use only "A" and "B" and "C" and "D"), results in a smaller set than the total patient population we are trying to emulate, i.e., under-inclusion. In some embodiments, over-inclusions may be weighted differently than under-inclusions for the purpose of determining how well a synthesized population represents a full patient population. In some embodiments, a higher degree of specificity is preferred over greater quantity, so over-inclusion would be weighted to discourage its occurrence relative to under-inclusion.

After embodiments simulate various combinations of patient population codes and/or the associated patient criteria, a synthesis of the codes can be provided (e.g., displayed) to allow both experts and non-experts to determine which specific factors drove the majority of the population selection. For example, it may become apparent that a cohort sharing sixteen patient criteria may turn out to have three patient criteria that determined the majority of population selection. Such determination is common in many population selections.

A simulation may proceed as follows. First, a user defines cohort criteria such as an age band or treatment (i.e., examples of controlled variables of the simulation), which are applied to the population in different sequences. Suppose that there are a total of "N" criteria (N a positive integer). It is well known from combinatorial mathematics that the number of permutations of N items is N! (i.e., N factorial). However, not all of the N criteria may be significant, e.g., N−1 or N−2 (or fewer) criteria may produce acceptable results, meaning that (N−1)! and (N−2)! permutations (as well as lesser numbers of permutations) may also need to be analyzed. The total number of permutations may be as large as $\Sigma_{i=1}^{i=N-1}$ (N−i)!. Because thirty or more of such criteria may be used in the definition of a cohort (i.e., N>=30), comprehensive manual testing of potential sequences is impractical.

A system in accordance with an embodiment of the present disclosure determines a cohort group for a predetermined number of criteria and order of application of the criteria. The embodiments then log the resulting cohort group (e.g., number of patients) associated with each of the different sequences that were chosen. At the conclusion of the simulation, one or more reduced sets of criteria may be outputted in order to produce the final cohort. Several top options may be presented to offer a tradeoff between the coverage and number of criteria. For example, if four factors produce 99% coverage and five factors produce 99.5% coverage, both may be presented to a human researcher or analyst for consideration. A sequence under test may be deemed to be good enough if the cohort produced by the sequence under test is sufficiently close in membership (e.g., by comparison of population numbers) to a cohort produced by consideration of all N criteria.

Embodiments in accordance with the present disclosure automate the synthesis of a population of patients under study along with the calculation of inferred or deduced selection criteria, and display the population and selection criteria graphically along with key information about the inferred or deduced selection criteria. Embodiments advance access to insights from large healthcare datasets for non-experts, and facilitate unlocking use of these insights regarding the data, to improve healthcare efficiency.

FIG. 1 depicts a system 100 according to an embodiment of the present disclosure. The system 100 may include a communication network 108 that is in communication with computing terminal 112. Exemplary types of external communication devices 112 include, without limitation, desktop Personal Computers (PCs), laptops, netbooks, tablets, thin clients, other smart computing devices, and the like that are accessible via a network. The communication link may operate by methods or protocols such as Ethernet, Wi-Fi, and so forth. The computing power of computing terminal 112 may be used at least in part to manage communications with other portions of system 100 described below.

The communication network 108 may be packet-switched and/or circuit-switched. An exemplary communication network 108 includes, without limitation, a Wide Area Network (WAN), such as the Internet, a Public Switched Telephone Network (PSTN), a Plain Old Telephone Service (POTS) network, a cellular communications network, or combinations thereof. In one configuration, the communication network 108 is a public network supporting the TCP/IP suite of protocols.

System 100 may further include server 144, which is coupled to communication network via transceiver 146. Transceiver 146 may support well-known communication or networking protocols such as Ethernet, Wi-Fi, and so forth. Server 144 may be capable of hosting and/or executing one or more application programs 152 ("apps" or "applications"). Server 144 may be a software-controlled system including a processor 154 coupled to a tangible memory 156. Memory 156 may comprise random access memory (RAM), a read-only memory (ROM), or combinations of these and other types of electronic memory devices. Memory 156 may be used for various purposes such as to store code (e.g., application programs 152) and working memory used by processor 154. Various other server 144 components such as a communication interface modules, power management modules, etc. are known by persons of skill in the art of computer design, but are not depicted in FIG. 1 in order to avoid obscuring the main elements of system 100.

Server 144 may be coupled to a database 162, either directly or through communication network 108 as illustrated in FIG. 1. Database 162 may also be separate from server 144 (as illustrated in FIG. 1), or be incorporated into server 144. Database 162 may be used to store an available universe of patient data (e.g., the GPRD). Database 162 may represent a plurality of physically dispersed databases that are communicatively coupled together.

The elements of system 100 are shown in FIG. 1 for purposes of illustration only and should not be construed as limiting embodiments of the present invention to any particular arrangement of elements. Various other system components such as a gateway, a firewall, etc. are known by persons of skill in the art of computer networking, but are not depicted in FIG. 1 in order to avoid obscuring the main elements of system 100.

Figure 2:
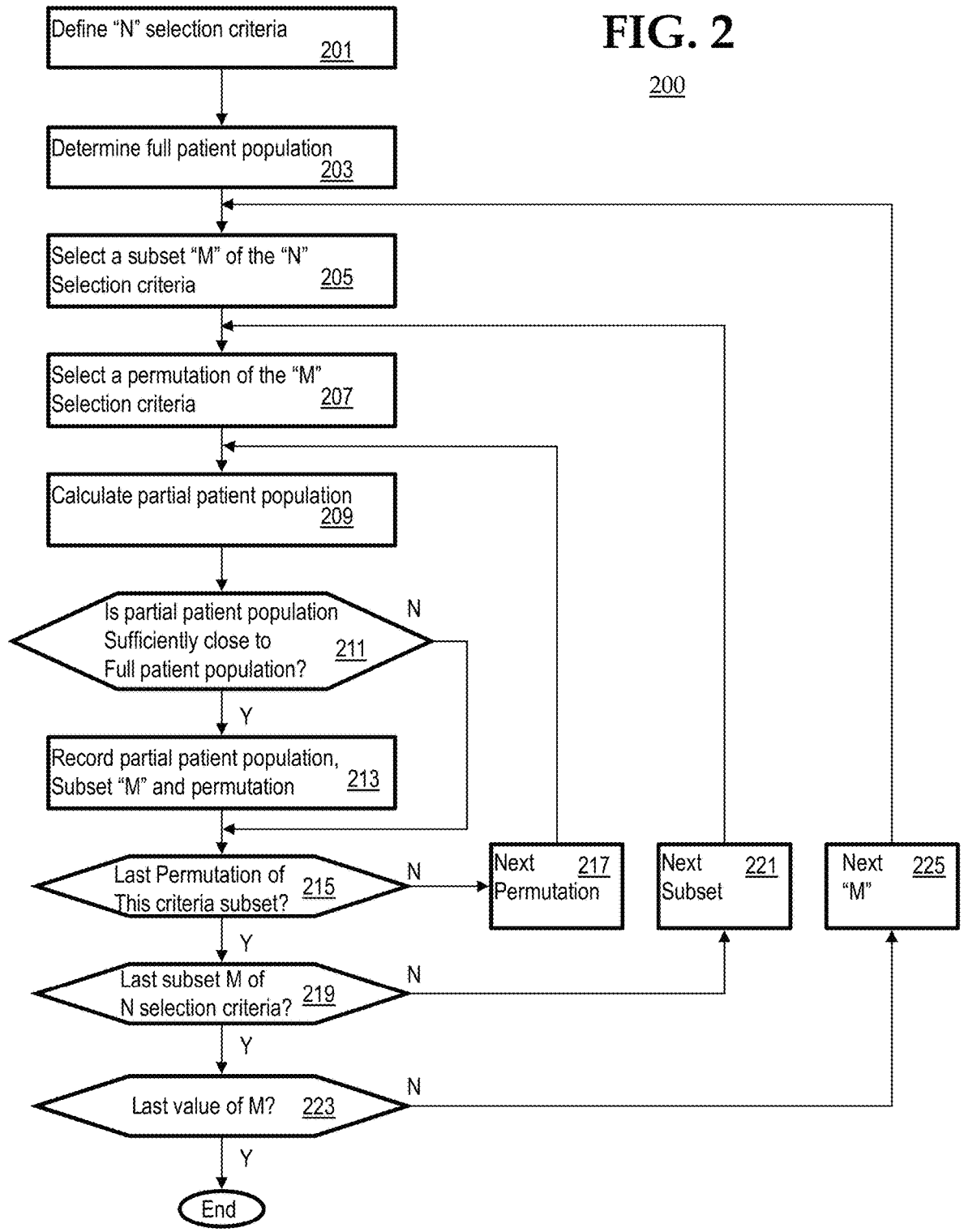
FIG. 2 depicts a method according to an embodiment of the present disclosure.

FIG. 2 illustrates a method 200 to operate system 100, in accordance with an embodiment of the present disclosure. Method 200 may proceed as follows. At step 201, a researcher or user of system 100 (generically, "user") may access system 100 from computing terminal 112 in order to define a selection criteria (i.e., a scenario) as part of a study. Without loss of generality, assume that there are "N" criteria.

Next, control of method 200 transitions to step 203 at which the scenario will be run (e.g., by the user at computing terminal 112) in order to determine a full patient population that satisfies the selection criteria. After this step, an automated synthesis process may be initiated (e.g., by a user). Computations may be performed by server 144 using data read from database 162.

Next, control of method 200 transitions to step 205, which begins the automatic synthesis process. The steps of the automatic synthesis process are encoded by software commands stored in memory 156 (e.g., as one or more apps 152), and are carried out by processor 154 performing actions as commanded by app 152.

The automated synthesis process beginning at step 205 and through step 225 will test various subsets and permutations of the N selection criteria, and record which subsets and permutations thereof of the N selection criteria produces a partial patient population that is sufficiently close to the full patient population. A comprehensive analysis may analyze every possible subset and permutation thereof of the N selection criteria, and will find a globally optimal solution. A disadvantage of a comprehensive analysis is that the simulation may take a long time to run. A selective analysis may analyze selected subsets and permutations thereof of the N selection criteria. An advantage of the selective analysis is that it is faster but a disadvantage is that is may miss finding the globally best solution.

"Partial" patient population refers to an observation that a patient population produced by omitting some of the N selection criteria in general will be different than a patient population produced by all N selection criteria. For example, if the omitted selection criterion had been specified by a Boolean "AND", then the partial patient population will be larger than the full patient population. If the omitted selection criterion had been specified by a Boolean "OR", then the partial patient population will be smaller than the full patient population. "Coverage" as used herein is a figure of merit that may refer to how close the partial patient population comes to the full patient population. Coverage may be calculated by one or more statistics, such as what percentage of the full patient population is included (or not included) in the partial patient population, and/or what percentage of the partial patient population is included (or not included) in the full patient population.

The automated synthesis process may proceed in one of several ways. For example, in an ascending method, the synthesis process may begin with small subsets and progressively analyze larger subsets of the N selection criteria. In a descending method, the synthesis may begin with an (N−1)-member subset of the selection criteria, analyzing all possible permutations thereof, and then moving on to progressively smaller subsets thereof. Ascending and descending methods may be used with both comprehensive and partial analysis.

For example, an ascending method may begin with calculating coverage for each of the N selection criteria individually. Any coverages that meet or exceed a threshold level of coverage may cause a signal to be raised (e.g., by an alert module or the like), which may trigger recording to memory of the coverage and corresponding subset and permutation of selection criteria that produced the coverage. Alternatively, only the K-best coverages (K≥1) calculated during the entire simulation may be retained. During the running of the simulation, detection of one of the K-best coverages up to that point in the simulation may cause a signal to be raised, which may trigger recording to memory of the coverage and corresponding subset and permutation of selection criteria that produced the coverage. A record of the K-best coverages may be maintained as a running record that is updated as necessary at the end of testing each subset and permutation, or may be calculated at the end of the entire simulation.

The signals may also be used as an alert to the human analyst who is responsible for the simulation. Having available more than one sufficiently acceptable permutation of selection criteria may be useful at the conclusion of the simulation in order for a human analyst to study further the appropriate selection criteria. The human analyst may later change the selection criteria for a new simulation. The human analyst may select an acceptable subset of criteria and permutation based upon considerations not considered or captured by the simulation.

After each of the N selection criteria have been analyzed one at a time, the ascending method may then continue by analyzing every possible pair of the N selection criteria. For example, in a comprehensive ascending method, if each of the N selection criteria are denoted $C_n$, $1 \leq n \leq N$, then each combination and permutation of pairs $(C_i, C_j)$ $\forall 1 \leq i \leq N$, $1 \leq j \leq N$, $i \neq j$ is analyzed, and any coverages and corresponding criteria that meet or exceed a threshold level of coverage may be recorded. After all possible combinations and permutations of pairs $(C_i, C_j)$ are analyzed, the comprehensive ascending method may continue by analyzing all possible combinations and permutations of triplets $(C_i, C_j, C_k)$ of the N selection criteria. This process continues until all possible combinations and permutations of subsets of size (N−1) elements are analyzed.

An ascending method may be used with a partial analysis. For example, after a predetermined number of stages, the subset and permutation producing the best coverage may be outputted as a partial result. The criteria forming the partial result may be removed from further consideration, and the rest of the remaining criteria may be analyzed to find the best additional coverage from the remaining criteria. For example, if after the third stage the best subset and permutation of criteria is ($C_5$, $C_1$, $C_2$), then criteria $C_1$, $C_2$, $C_5$ may be removed from further consideration and analysis will continue using only criteria $C_3$, $C_4$, and $C_6 \ldots C_N$. In this example, a subset of size J=3 of the original N criteria has been identified, and an intermediate permutation ($C_5$, $C_1$, $C_2$) of the J criteria has been identified. The J criteria have been removed from further consideration as being an intermediate result, and the analysis may proceed using the N−J remaining criteria (i.e., $C_3$, $C_4$, and $C_6 \ldots C_N$). Additional intermediate results may also be taken of the N−J remaining criteria. At the end of the analysis, intermediate result(s) may be concatenated with the results based upon the N−J remaining criteria, to produce overall results. Other methods of pruning may also be used.

A descending method may begin by analyzing all possible permutations of smaller and smaller subsets of (N−1) selection criteria and fewer. There is no need to examine permutations of all N selection criteria, since it is known that each such permutation will result in the full patient population. For example, for (N−1) selection criteria, the set of $C_1 \ldots C_N$ criteria (except for the one the removed criterion) forms a subset, and the subset may be permuted and a coverage may be calculated for each permutation of the subset. In other respects, the descending method may operate similarly to the ascending method as described above.

Since even for a large number of criteria $C_N$ it is likely that only a relatively small number of criteria may be used to provide an acceptable level of coverage, an ascending method is likely to be computationally more efficient, because the smallest subset of criteria producing an acceptable coverage is likely to be found more quickly.

Returning again to FIG. 2, method 200 at step 205 will select a subset "M" of the N selection criteria. For an ascending method, step 205 begins with M=1. For a descending method, step 205 begins with M=N−1.

Next, control of method 200 transitions to step 207, at which a permutation of the M selection criteria is selected. There will be M factorial number of permutations from which to select.

Next, control of method 200 transitions to step 209, at which a partial patient population for the selected permutation of M selection criteria is calculated.

Next, control of method 200 transitions to step 211, at which a coverage resulting from the selected permutation of M selection criteria is calculated. The coverage is a statistic that indicates how close the partial patient population is to the full patient population. The statistic may be in the form of, e.g., a percentage of overlap or non-overlap, a mathematical correlation, and so forth. The statistic may further show a relative contribution to coverage from each of the criteria. The coverage is then compared to a threshold, for example, that at least 99.5% of full patient population is included in the partial patient population. If the coverage exceeds the threshold then control of method 200 transitions to step 213, otherwise control of method 200 transitions directly to step 215.

At step 213, a record may be stored in memory 156 of the coverage and the selected permutation of the M selection criteria that produced the coverage. In some embodiments, all permutations that exceed the threshold may be recorded and retained. In some embodiments, only the highest K permutations (K≥1 may be retained. At the conclusion of step 213, control of method 200 transitions to step 215.

At decision step 215, a decision is made and a resulting signal is set to indicate whether the last permutation for the present set of M selection criteria that were selected at step 207 has been analyzed. If the outcome of decision step 215 is negative, then control of method 200 transitions to step 217 at which a next permutation for the present set of M selection criteria is selected for analysis to calculate a partial patient population. For example, if N=5 and M=3, and if the present subset and permutation is ($C_2$, $C_1$, $C_4$), then the next permutation may be ($C_2$, $C_4$, $C_1$). At the conclusion of step 217, control of method 200 reverts to step 209. If the outcome of decision step 215 is positive, then control of method 200 transitions to step 219.

At decision step 219, a decision is made and a resulting signal is set to indicate whether the last subset M of the N selection criteria have been considered and analyzed. If the outcome of decision step 219 is negative, then control of method 200 transitions to step 221 at which a next subset M of the N selection criteria is considered. For example, if N=5 and M=3, and if the present subset is ($C_1$, $C_2$, $C_4$), then the next subset may be ($C_1$, $C_2$, $C_5$). At the conclusion of step 221, control of method 200 reverts to step 207. If the outcome of decision step 219 is positive, then control of method 200 transitions to step 223.

At decision step 223, a decision is made and a resulting signal is set to indicate whether the last value of M has been considered. If the outcome of decision step 223 is negative, then control of method 200 transitions to step 225 at which a next value of M is considered. For example, if N=5 and M=3, and all permutations of the five criteria taken three at a time have been considered, then at step 225 the next value of M may be considered. For an ascending method, the next value after M=3 would be M=4. For a descending method, the next value after M=3 would be M=2. At the conclusion of step 225, control of method 200 reverts to step 205. If the outcome of decision step 223 is positive, then method 200 ends.

Figure 3:
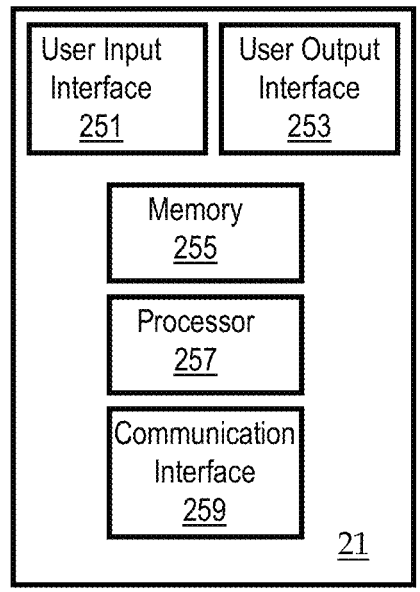
FIG. 3 illustrates components of a computing terminal.

FIG. 3 illustrates components of computing terminal 112. As illustrated, in this embodiment, computing terminal 112 is a typical desktop or mobile computing device having basic functions. Computing terminal 112 has a user input interface 251 for receiving input from a user (e.g., a keyboard, touchscreen and/or microphone), and a user output interface 253 is provided for presenting information visually or audibly to the user. Computing terminal 112 also includes memory 255 for storing an operating system that controls the main functionality of computing terminal 112, along with a number of applications that are run on computing terminal 112, and data. A processor 257 executes the operating system and applications. Computing terminal 112 may have a unique hardware identification code that permits identification of computing terminal 112 (e.g., a medium access control (MAC) address). At least a portion of memory 255 may be encrypted. A communications interface 259 permits communications with communication network 108, e.g., by way of an Ethernet or Wi-Fi interface. A user may use computing terminal 112 in order to control the practice of embodiments described herein, and to receive and review results of the embodiments.

FIG. 4 illustrates a cohort detailed description 400 that system 100 may present to a user, e.g., at computing terminal 112, which shows various selection criteria (i.e., filters) chosen by a user for a cohort study and other information relevant to the cohort study. Application of all of these selection criteria would produce a full patient population.

FIG. 5 illustrates a user interface 500 that system 100 may present to a user, e.g., at computing terminal 112, which shows the result of a manual synthesis of selection criteria, and running a scenario using all of the selection criteria. User interface 500 is provided for illustration only, and does not necessarily correspond specifically to cohort detailed description 400. User interface 500 illustrates a full patient population using all of the selection criteria, including a percentage inclusion for each criterion. The percentages of inclusion provide to a human analyst an understanding of the relative importance of various selection criteria to the overall full patient population. If a human analyst wanted to reduce the number of criteria, while providing a partial patient population that is sufficiently close to the full patient population, an understanding of the relative importance of various selection criteria would be helpful if the process simply were, e.g., a greedy process that selected the N-best (i.e., highest percentage) criteria. However, this would give no insight as to the order in which to apply criteria, and furthermore a greedy process may miss a globally optimal solution. Embodiments in accordance with the present disclosure can overcome this problem by comprehensively studying all possible number of factors, selections of factors, and permutations of factors.

Embodiments of the present invention include a system having one or more processing units coupled to one or more memories. The one or more memories may be configured to store software that, when executed by the one or more processing unit, allows practice of embodiments described herein, including at least in FIG. 2 and related text.

The disclosed methods may be readily implemented in software, such as by using object or object-oriented software development environments that provide portable source code that can be used on a variety of computer or workstation platforms. Alternatively, the disclosed system may be implemented partially or fully in hardware, such as by using standard logic circuits or VLSI design. Whether software or hardware may be used to implement the systems in accordance with various embodiments of the present invention may be dependent on various considerations, such as the speed or efficiency requirements of the system, the particular function, and the particular software or hardware systems being utilized.

While the foregoing is directed to embodiments of the present invention, other and further embodiments of the present invention may be devised without departing from the basic scope thereof. It is understood that various embodiments described herein may be utilized in combination with any other embodiment described, without departing from the scope contained herein. Further, the foregoing description is not intended to be exhaustive or to limit the invention to the precise form disclosed. Modifications and variations are possible in light of the above teachings or may be acquired from practice of the invention. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the invention unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. § 112, ¶6, and any claim without the word "means" is not so intended.

What is claimed is:

1. A machine-implemented method to select a subset of selection criteria with which to identify a population for membership in a study cohort, comprising:

identifying a full population of patients having characteristics that satisfy N selection criteria, wherein N is an integer greater than 29;

defining all possible subsets of the N selection criteria;

identifying all possible permutations of each of the subsets of the selection criteria, wherein the permutations include re-orderings of the selection criteria of the respective subsets of the selection criteria;

determining, for each permutation of each subset, a partial population of patients having characteristics that satisfy the ordering of the subset of the selection criteria of the permutation;

recording each partial population that matches the identified full population to within a predetermined threshold, including recording the subset of selection criteria, the ordering of the subset of selection criteria, and a relative significance of each criterion of the subset of the selection criteria;

selecting one or more of the recorded partial populations that have a fewest number of the selection criteria; and graphically displaying each selected partial population, the corresponding subset of selection criteria, and the relative significance of each criterion of the subset of selection criteria.

2. The method of claim 1, further comprising omitting a portion of the selection criteria for membership in the study cohort.

3. The method of claim 1, further comprising:

incrementing a number of the selection criteria per subset from M=1 towards M=N−1; and performing the defining, the identifying, the determining, and the recording for each of multiple values of M.

4. The method of claim 1, further comprising:

decrementing a number of the selection criteria per subset from M=N−1 towards M=1; and performing the defining, the identifying, the calculating, and the recording for each of multiple values of M.

5. An apparatus to select a subset of selection criteria with which to identify a population for membership in a study cohort, comprising a processor configured to:

identify a full population of patients having characteristics that satisfy N selection criteria, wherein N is an integer greater than 29;

define all possible subsets of the N selection criteria;

identify all possible permutations of each of the subsets of the selection criteria, wherein the permutations include re-orderings of the selection criteria of the respective subsets of the selection criteria;

determine, for each permutation of each subset, a partial population of patients having characteristics that satisfy the ordering of the subset of the selection criteria of the permutation;

record each partial population that matches the identified full population to within a predetermined threshold, including to record the subset of selection criteria, the ordering of the subset of selection criteria, and a relative significance of each criterion of the subset of the selection criteria;

select one or more of the recorded partial populations that have a fewest number of the selection criteria; and graphically display each selected partial population, the corresponding subset of selection criteria, and the relative significance of each criterion of the subset of selection criteria.

6. The apparatus of claim 5, wherein the processor is further configured to:

omit a portion of the selection criteria for membership in the study cohort.

7. The apparatus of claim 5, wherein the processor is further configured to:

increment a number of the selection criteria per subset from M=1 towards M=N−1; and perform the defining, the identifying, the determining, and the recording for each of multiple values of M.

8. The apparatus of claim 5, wherein the processor is further configured to:

decrement a number of the selection criteria per subset from M=N−1 towards M=1; and perform the defining, the identifying, the calculating, and the recording for each of multiple values of M.

9. A non-transitory computer readable medium encoded with a computer program that comprises instructions to cause a processor to:

identify a full population of patients having characteristics that satisfy N selection criteria, wherein N is an integer greater than 29;

define all possible subsets of the N selection criteria;

identify all possible permutations of each of the subsets of the selection criteria, wherein the permutations include re-orderings of the selection criteria of the respective subsets of the selection criteria;

determine, for each permutation of each subset, a partial population of patients having characteristics that satisfy the ordering of the subset of the selection criteria of the permutation;

record each partial population that matches the identified full population to within a predetermined threshold, including to record the subset of selection criteria, the ordering of the subset of selection criteria, and a relative significance of each criterion of the subset of the selection criteria;

select one or more of the recorded partial populations that have a fewest number of the selection criteria; and graphically display each selected partial population, the corresponding subset of selection criteria, and the relative significance of each criterion of the subset of selection criteria.

10. The non-transitory computer readable medium of claim 9, further comprising instructions to cause the processor to:

omit a portion of the selection criteria for membership in the study cohort.

11. The non-transitory computer readable medium of claim 9, further comprising instructions to cause the processor to:

increment a number of the selection criteria per subset from M=1 towards M=N−1; and perform the defining, the identifying, the determining, and the recording for each of multiple values of M.

12. The non-transitory computer readable medium of claim 9, further comprising instructions to cause the processor to:

decrement a number of the selection criteria per subset from M=N−1 towards M=1; and perform the defining, the identifying, the calculating, and the recording for each of multiple values of M.

\* \* \* \* \*

UNITED STATES PATENT AND TRADEMARK OFFICE
CERTIFICATE OF CORRECTION

PATENT NO. : 11,282,589 B2
APPLICATION NO. : 14/506961
DATED : March 22, 2022
INVENTOR(S) : Haskell et al.

It is certified that error appears in the above-identified patent and that said Letters Patent is hereby corrected as shown below:

In the Specification

Column 11, Line 59, after "that" and before "may", replace "is" with "it".

Signed and Sealed this
Seventeenth Day of May, 2022

Katherine Kelly Vidal
*Director of the United States Patent and Trademark Office*